(12) United States Patent
Muesch et al.

(10) Patent No.: US 7,166,179 B2
(45) Date of Patent: Jan. 23, 2007

(54) ADHESIVE BANDAGE PAD MODULE AND METHOD FOR MAKING AND APPLYING ADHESIVE BANDAGE PADS TO A WEB

(76) Inventors: Edward Muesch, 1428 Summit Ave., Toms River, NJ (US) 08753; Charles Lee Adams, 21 Olden Dr., Flemington, NJ (US) 08822; John Damiani, 8 Sweney Ct., Neshanic Station, NJ (US) 08853; Phil DeSalvo, 31 Glengarry Way, Cranbury, NJ (US) 08512

( * ) Notice: Subject to any disclaimer, the term of this patent is extended or adjusted under 35 U.S.C. 154(b) by 234 days.

(21) Appl. No.: 10/266,554

(22) Filed: Oct. 8, 2002

(65) Prior Publication Data

US 2003/0084992 A1    May 8, 2003

Related U.S. Application Data

(62) Division of application No. 09/471,990, filed on Dec. 23, 1999, now Pat. No. 6,484,778.

(51) Int. Cl.
  *B32B 37/00*   (2006.01)
  *B26D 7/00*    (2006.01)
  *A61F 13/00*   (2006.01)

(52) U.S. Cl. .................. 156/265; 156/302; 409/51; 604/358

(58) Field of Classification Search ................ 156/265, 156/299, 300, 301, 302, 512, 519; 604/358; 409/51

See application file for complete search history.

(56) References Cited

U.S. PATENT DOCUMENTS

| | | | | |
|---|---|---|---|---|
| 2,642,116 A | * | 6/1953 | Fisher et al. | 156/518 |
| 2,794,479 A | * | 6/1957 | Ganz | 156/443 |
| 3,245,855 A | | 4/1966 | Stenvall | 156/152 |
| 3,708,375 A | * | 1/1973 | Kistner | 156/552 |
| 3,879,246 A | | 4/1975 | Walker | 156/265 |
| 4,642,150 A | | 2/1987 | Stemmler | 156/164 |
| 5,735,443 A | | 4/1998 | Ring | 225/4 |
| 6,207,001 B1 | | 3/2001 | Steidinger et al. | 156/264 |
| 6,602,285 B1 | | 8/2003 | Von Oepen | 623/1.17 |

FOREIGN PATENT DOCUMENTS

WO    WO 96/36487    11/1996

* cited by examiner

*Primary Examiner*—Linda Gray

(57) ABSTRACT

An adhesive bandage pad module, and a method of making adhesive bandage pads, are disclosed. The adhesive bandage pad module, and method of making an adhesive bandage pad, include a servo motor which rotates a knife roll, a transfer roll, and an infeed assembly, a continuous pad strip fed to the infeed assembly, a knife roll and a blade that cuts the continuous pad strip against an anvil, that tangentially contacts the knife roll, on the knife roll. In the module, the amount of pressure exerted by the blade upon the anvil, and transferring of the cut pad onto an adhesive backing on the transfer roll are controlled.

4 Claims, 4 Drawing Sheets

ADHESIVE BANDAGE PAD MODULE AND METHOD FOR MAKING AND APPLYING ADHESIVE BANDAGE PADS TO A WEB

The present application is a division of U.S. patent application Ser. No. 09/471,990, filed Dec. 23, 1999, now issued as U.S. Pat. No. 6,484,778.

BACKGROUND OF THE INVENTION

1. Field of the Invention

The present invention is directed generally to a method and apparatus for making adhesive bandages and, more particularly, to an adhesive bandage pad module and a method for making adhesive bandage pads.

2. Description of the Background

Adhesive bandage pads have long been used to provide a protective cover for a wound, while isolating the wound from the adhesive used to fasten the bandage to the skin. One type of bandage has a continuous narrow strip of pad material placed transversely across the center of a continuous strip of adhesive backing, and the pad and backing material is then cut along the width of the adhesive backing. This method produces a bandage with a pad that extends to the edges of the adhesive backing. This type of pad is known as a full width pad. Manufacture of a full width pad bandage is straight-forward and known in the art.

A second design places discrete pads onto the center of an adhesive backing. This type of pad, known in the art as an "island pad," provided adhesive at the edges of the pad. Island pad bandages are currently produced using a "cut and place" method, wherein individual pads are first cut from a strip and then mechanically placed with precision onto an adhesive strip. The cut and place method of making island pads has proven relatively slow and inaccurate. In response, some suppliers moved to "full width" bandages, in order to achieve improved production efficiency. Additionally, "full width" bandage machines, as well as prior "island pad" machines, were often not removable, and thus were difficult to maintain.

Therefore, the need exists for a module and method that can quickly and accurately cut an island pad and transfer it to an adhesive backing to create an adhesive bandage pad at a production efficiency comparable to that achieved in connection with "full width" bandages, and for a module that is removable to provide ease of maintenance.

BRIEF SUMMARY OF THE INVENTION

The present invention is directed to an adhesive bandage pad module. The adhesive bandage pad module includes an infeed assembly which receives a continuous pad strip, and a knife roll having a plurality of blades placed laterally thereon. The knife roll receives the continuous pad strip from the infeed assembly. An anvil tangentially contacts the knife roll and presses the continuous pad strip into contact with the knife roll at the tangency. The knife roll then carries the cut pad to a transfer roll. The transfer roll carries an adhesive backing to receive a cut pad from the knife roll. A gear aligner allows for positioning of the cut pad from the knife roll to the transfer roll. At least one servo motor drives the infeed assembly, the knife roll, and the transfer roll. In a preferred embodiment, the anvil is not driven, thereby reducing wear from knife blade strikes. In one embodiment, a force adjustor is used to control the amount of force exerted by the anvil against the knife roll during cutting.

The present invention also includes a method of making an adhesive bandage pad. The method of making an adhesive bandage pad includes rotating a servo motor, which servo motor rotates at least one of a knife roll, a transfer roll, and an infeed assembly; feeding a continuous pad strip to the infeed assembly; cutting the continuous pad strip against the anvil with a blade located on the knife roll; and transferring the cut pad onto an adhesive backing. In one embodiment, the method also includes controlling an amount of pressure exerted by the blade upon the anvil during the cutting step.

The present invention solves problems experienced with the prior art because the use of a servo motor prevents the slow speed and excessive skewing encountered during use of one or more clutch driven motors. Further, the use of a force adjustor improves accuracy in the cutting of the pads. Thus, the present invention offers speed approaching that of full width pad production for island pad production, while providing ease of maintenance due to a stand-alone pad module. Those and other advantages and benefits of the present invention will become apparent from the detailed description of the invention hereinbelow.

BRIEF DESCRIPTION OF THE SEVERAL VIEWS OF THE DRAWINGS

For the present invention to be clearly understood and readily practiced, the present invention will be described in conjunction with the following figures, wherein.

DETAILED DESCRIPTION OF THE INVENTION

It is to be understood that the figures and descriptions of the present invention have been simplified to illustrate elements that are relevant for a clear understanding of the present invention, while eliminating, for purposes of clarity, many other elements found in a typical adhesive bandage pad module. Those of ordinary skill in the art will recognize other elements desirable for implementing the present invention. However, because such elements are well known in the art, and because they do not facilitate a better understanding of the present invention, a discussion of such elements is not provided herein.

Figure 1:
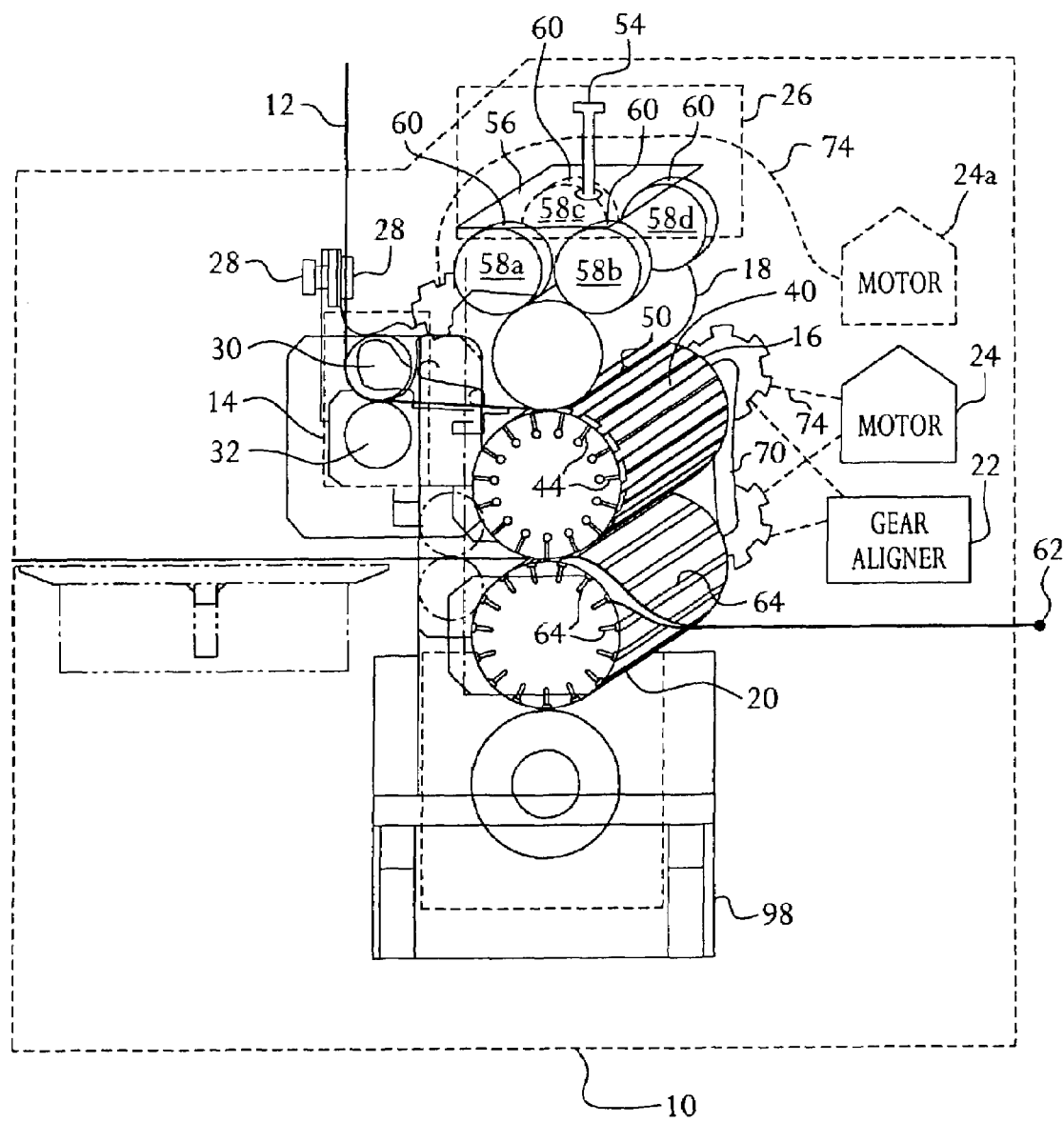
FIG. 1 is a schematic diagram illustrating an adhesive bandage pad module.

FIG. 1 is a schematic diagram illustrating an adhesive bandage pad module 10, including a continuous pad strip 12, an infeed assembly 14, a knife roll 16, an anvil 18, a transfer roll 20, a gear aligner 22, and at least one motor 24, and may include a force adjustor 26.

The infeed assembly 14 receives the continuous pad strip 12. In one embodiment of the present invention, the continuous pad strip 12 is guided into the infeed assembly 14 by at least two manually adjusted guide plates 28. The continuous pad strip may be formed of a woven or non-woven fabric sheet, a woven or non-woven fibrous sheet, or any material used in the art, or new to the art, for forming bandage pads, or may be formed of a medicated hydrogel. The infeed assembly 14 is properly sized to receive the horizontal, non-continuous portion of the continuous pad strip 12. This width, in a typical embodiment, may be ¾", but may be varied to provide adhesive bandages of varying widths. For example, the width of the strip 12 may be from about ¼" to about 9", and preferably from about ½" to about 5", and more preferably from about ½" to about 4".

In one embodiment, infeed assembly 14 includes a moving top belt 30 and a stationary drag plate 32. The continuous pad strip 12 is fed into the module 10 by the moving top belt 30, and is pressed between the top belt 30 and the stationary drag plate 32. In an alternative embodiment, infeed assembly 14 includes a moving top belt 30 and a moving bottom belt. The moving bottom belt preferably moves at the same speed as the moving top belt 30, to allow for the continuous pad strip 12 to be pressed there-between and carried by the infeed assembly 14 with minimal friction. In this alternative embodiment, the continuous pad strip 12 may have placed thereon anointment, and, where a therapeutic hydrogel or ointment is present, the moving bottom belt grips at least one of the two non-continuous edges of the continuous pad strip 12.

Figure 1A:
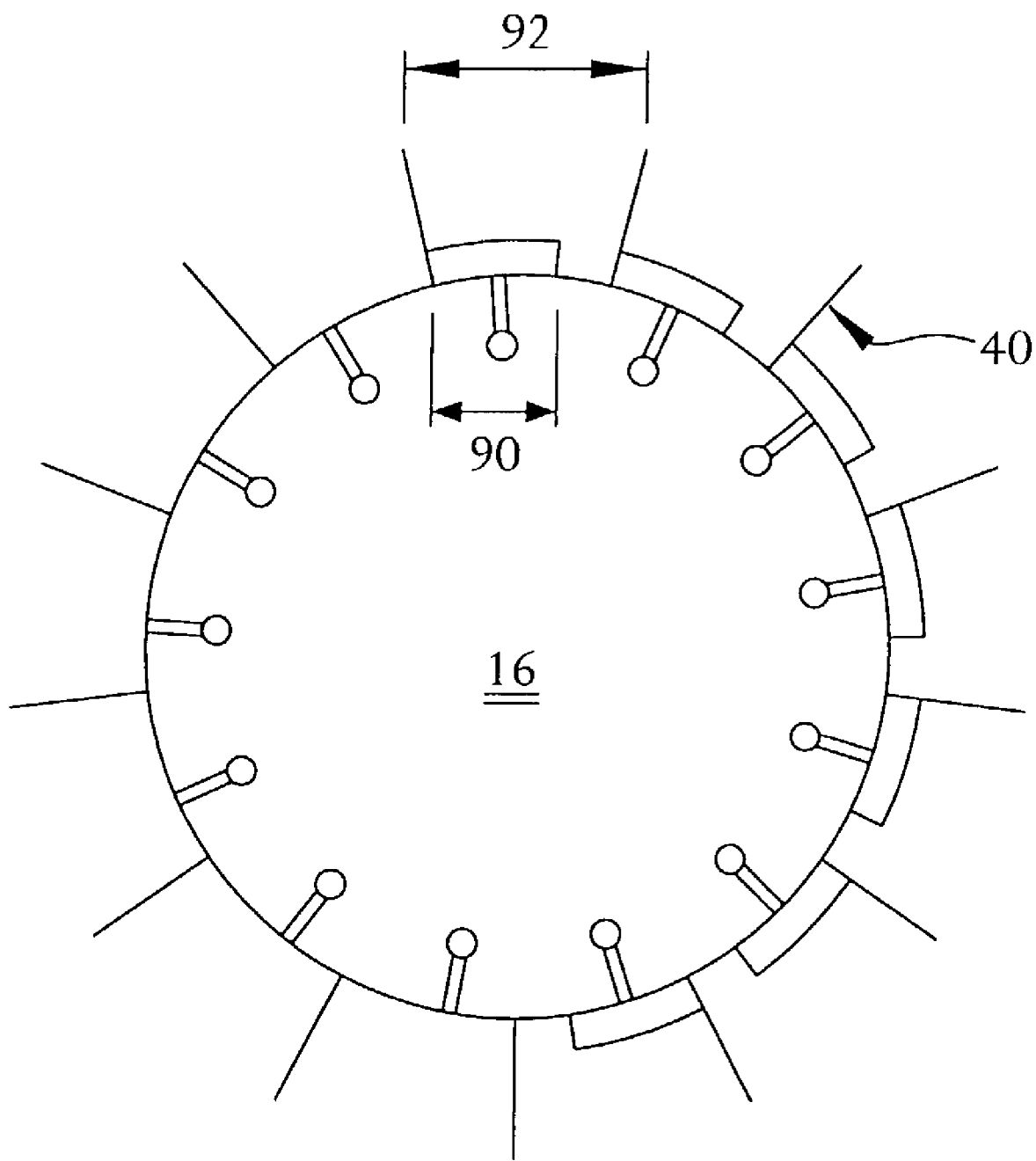
FIG. 1A is a schematic diagram illustrating the correspondence of cutting length and placement length.

The knife roll 16 is placed in the pad module 10 along the path of the continuous pad strip 12 following the infeed assembly 14. The knife roll 16 may be housed at its rotating ends within a bearing housing. The knife roll 16 has a plurality of blades 40 placed laterally thereon, and receives the continuous pad strip 12 from the infeed assembly 14. The plurality of blades 40 on the knife roll 16 are placed thereon in specific increments around the circumference of the knife roll 16, which increments correspond to a pad placement length. The cutting length will depend on the rate of the infeed motor, rather than on the distance between the knife blades 40. As an example, in the above embodiment wherein the strip width is ¾" wide and a ½" wide pad is desired, the knife blades 40 would be placed ¾" apart along a circumferential distance around the knife roll 16 and the infeed assembly would feed the pad to achieve a ½" width. Assuming a ¾" width pad material is used, a ¾"×½" pad would thereby be generated after cutting. This correspondence of cutting length 90 and placement length 92 is illustrated in FIG. 1A.

In one embodiment of the present invention, the knife roll 16 has vacuum holes 44 placed thereon adjacent to the knife blades 40. The vacuum holes 44 help maintain the pad 12 placement during cutting, and, after cutting, help properly align the cut pad during transfer from the knife roll 16 to the transfer roll 20. The vacuum holes 44 engage just before the anvil 18 contacts the knife roll 16, and disengage when the transfer roll 20 contacts the knife roll 16. In an alternative preferred embodiment, in addition to the vacuum holes 44, the knife roll 16 has thereon a textured silicon adhesive tape placed between the knife blades 40 to maintain pad placement during and following cutting. The tape may be, for example, TESA TAPE part #4863-FB-55-AF90.

The anvil 18 tangentially contacts the knife roll 16. The anvil 18 presses the continuous pad strip 12 into contact with the knife roll 16 at the tangent line 50. The anvil 18 is preferably not driven, and so is rotated only by the turning of the knife roll 16. Because the anvil 18 is not driven, it offers an almost infinite number of striking points for the knife blades 40, thereby prolonging the life of the anvil 18. In alternative embodiments, anvil 18 may be driven by an external motor or gear. The anvil 18 may be made of steel, or of any material suitable for use in the present invention.

The force adjustor 26 optionally controls the amount of force exerted on the continuous pad strip 12 between the anvil 18 and the knife roll 16. The force exerted is adjusted by the force adjustor 26 to be accurate and repeatable. The force may be measured and/or displayed on a gauge to a user, to allow user selection of a correct pressure. In an alternative embodiment, the pressure may be constantly adjusted using a programmable logic controller or a computer. In one embodiment of the present invention, the force adjustor 26 includes at least one adjustment screw 54, which at least one adjustment screw 54 is rotatably connected to cause the exertion of pressure on pressure plate 56, and at least two bearings 58. In a preferred embodiment, there are two screws 54. The pressure plate 56 is forced in a direction toward the anvil 18 upon turning of the at least one adjustment screw 54. The bearings 58 respond to a movement of the pressure plate 56 by exerting a force on the anvil 18 in the same direction as the movement of the pressure plate 56. Preferably, there are four bearings 58, and each bearing tangentially meets the anvil 18. The four bearings 58 are located such that the tangent lines 60 of two bearings 58b, 58c form a line which is parallel to a line passing through the tangent lines 60 of the two remaining bearings 58a, 58d. The at least one screw 54 shown in FIG. 1 is an adjustor 54, and is interchangeable with a hydraulic adjustment, a pneumatic adjustment, or a spring or series of springs.

In one embodiment, force adjustor 26 may be included as an EQUALIZER force adjustor manufactured by ADT (not shown) to equalize the force exerted on the bearings 58 to control the forces on the anvil 18. The EQUALIZER force adjustor is first grossly adjusted using hand knobs to initiate contact with the bearings 58, and is then fine tuned using an adjustment handle. In other alternative embodiments, a spring adjustment may be used as a force adjustor, which spring uses spring tension to push on the anvil 18; an air cylinder may be used in which the air pressure can be adjusted to vary the forces on the anvil 18; or a screw may be used to adjust a force transducer applying force to the anvil 18.

The transfer roll 20 tangentially contacts the knife roll 16, and receives a cut pad from the knife roll 16. In the preferred embodiment, a gear aligner, known in the art as a harmonic phaser 22, is used to position the knife roll 16 to the transfer roll 20. The gear aligner 22 is a gear driven device as is known and used in the art to ensure that two rolls are properly synchronized. Also fed onto the transfer roll 22, before receipt of the cut pad, is an adhesive backing 62. The adhesive backing is a preferably elastic, woven or non-woven, fabric or non-fabric material, and may be any material used in the art for adhesive bandage backing. In one embodiment of the present invention, the backing 62 is fed from a continuous source external to the pad module 10, and is fed adhesive side up. The cut pad is adhered to the backing 62 by the transfer roll 20. In a preferred embodiment of the present invention, the cut pad is smaller in width then the shortest length across the adhesive backing, thereby forming an island pad, surrounded by adhesive, on the adhesive backing 62.

In a preferred embodiment, transfer roll 20 is a rubber coated roll with grooves 64 spaced thereon. The grooves 64 are spaced to correspond to the location where the blades 40 from the knife roll 16 strike the transfer roll 20. Each groove 64 has a vacuum port therein. The vacuum port 64 remains engaged until the backing material 62, with the cut pad placed thereon, is to be released from the transfer roll 20. In an alternative embodiment, transfer roll 20 may be a vacuum conveyer belt.

The transfer roll 20 may be housed at its ends within a bearing housing. Because of the necessity of placing the bearing housing of the transfer roll 20 in close proximity to the bearing housing of the knife roll 16, thereby allowing the knife roll 16 to tangentially contact the transfer roll 20, spacers 70 may be placed between the bearing housings of the transfer roll 20 and the knife roll 16 to relieve friction and pressure on the respective bearing housings.

At least one motor 24 is used to drive the infeed assembly 14, the knife roll 16, and the transfer roll 20. In the preferred embodiment, one motor 24a is used to rotate the infeed assembly 14, and one motor 24 is used to rotate the knife roll 16 and the transfer roll 20. Alternatively, one motor may drive the infeed assembly 14, the knife roll 16, and the transfer roll 20. The motor 24 is preferably a servo motor 24, which servo motor 24 may be electrically tied 74 to the rotation of the infeed assembly 14, thereby ensuring high accuracy during starting and stopping of the line. A servo motor 24 provides improved precision, high speed operation, and variability of cut sizes without changes in mechanical parts. The infeed assembly 14, the knife roll 16, and the transfer roll 20 may be directly or indirectly connected to the servo motor 24, and directly or indirectly connected to one another, using a plurality of gears.

Figure 1B:
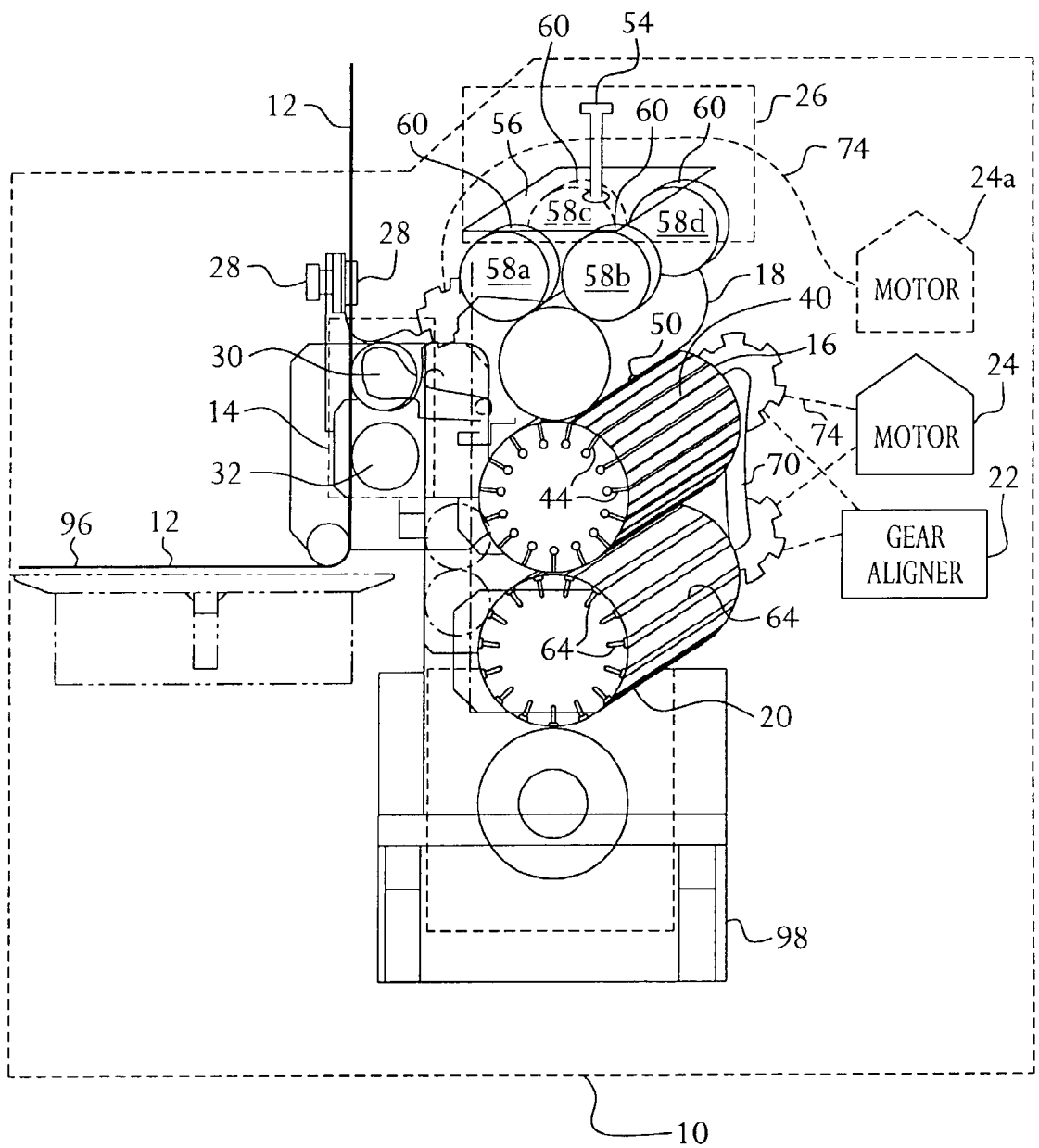
FIG. 1B is a schematic diagram illustrating an adhesive bandage pad module using an alternative path.

In a preferred embodiment of the present invention, the adhesive bandage pad module 10 is a removable module in a series of modules used to complete the entire bandage-making process. The removable module is mounted in a manner that allows for easy removability and maintenance, as is known in the art of modular manufacturing processes. The mounting may be done using a bracket 98, for example. Further, the adhesive band pad module 10 could be removed to allow a full width pad to be cut from the pad strip 12, or to allow pad strip 12 to follow another alternate web path. This circumventing could be performed, for example, by placing an additional idling roller at the input to the module, which additional roller would redirect the pad strip 12 away from knife roll 16. An example of this redirection is shown as FIG. 1B, and the alternate path is shown as path 96.

Figure 2:
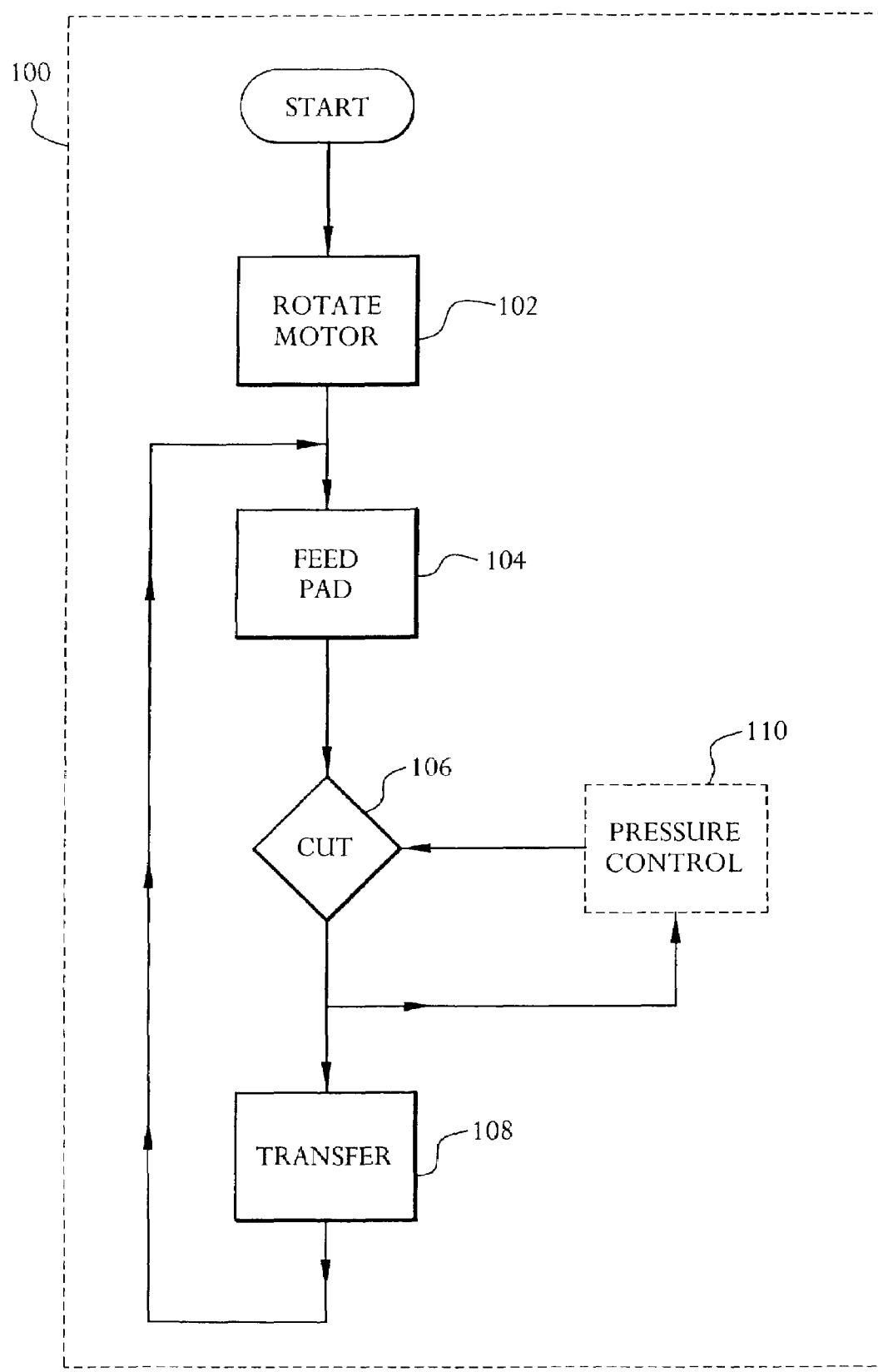
FIG. 2 is a block diagram illustrating a method of making adhesive bandage pads.

FIG. 2 is a block diagram illustrating a method of making and applying adhesive bandage pads to a bandage web 100. The method 100 includes the steps of rotating at least one motor 102, feeding a continuous pad strip to an infeed assembly 104, cutting the continuous pad strip 106, and transferring the cut pad to an adhesive backing 108, and may include the step of controlling the pressure 110 used to cut the continuous pad strip.

At step 102, a motor (e.g., motor 24) is rotated. In a preferred embodiment, there are two servo motors. A single servo motor may drive the knife roll 16 and the transfer roll 22, and a second servo motor may drive the infeed assembly 14.

At step 104, a continuous pad strip is fed to the infeed assembly. The strip passes through the infeed assembly and, in step 106, the continuous pad strip is cut against anvil 18 with a blade located on the knife roll. Finally, at step 108, the cut pad is transferred to an adhesive backing.

At optional step 110, the amount of pressure exerted by the blade upon the anvil during the cutting step 106 is controlled. In the preferred embodiment, the pressure is controlled substantially as disclosed hereinabove, such as by an Equalizer, a spring, a hydraulic adjustor, a pneumatic adjustor, or a screw adjustor.

The method of the present invention may also include removal of the adhesive bandage pad module from a manufacturing process by disconnecting a bracket, for example, or a redirection of the continuous strip to an alternate path not including the adhesive bandage pad module. These alternative embodiments of the method of the present invention operate substantially as discussed hereinabove with respect to FIGS. 1 and 1B.

Those of ordinary skill in the art will recognize that many modifications and variations of the present invention may be implemented. The foregoing description and the following claims are intended to cover all such modifications and variations.

What is claimed is:

1. A method of making and applying a bandage pad to a bandage web to form and adhesive bandage, comprising:
   rotating at least one servo motor, wherein said at least one servo motor rotates a knife roll having a plurality of blades thereon, a transfer roll, and an infeed assembly;
   feeding a continuous pad strip to the infeed assembly,
   cutting the continuous pad strip against an anvil with a blade located on the knife roll, said cutting forming individual bandage pads;
   carrying a cut pad to said transfer roll, said transfer roll being in contact with said knife roll;
   synchronizing the transfer of individual bandage pads from said knife roll to said transfer roll; and
   transferring the cut pad into an adhesive backing.

2. The method of claim 1, further comprising controlling an amount of pressure exerted by the blade upon the anvil during said cutting.

3. A method of making an adhesive bandage comprising an adhesive backing and a pad, comprising:
   feeding a continuous pad strip to an infeed assembly;
   rotating at least one motor, which at least one motor rotates a knife roll, a transfer roll, and the infeed assembly;
   cutting the continuous pad strip against an anvil with a blade located on the knife roll;
   controlling an amount of pressure exerted by the blade upon the anvil during said cutting;
   carrying a cut pad to said transfer roll, said transfer roll being in contact with said knife roll; and
   transferring the cut pad onto an adhesive backing;
   wherein controlling an amount of pressure is accomplished using a force adjuster, said force adjuster comprising an adjuster, a pressure plate connected to said adjuster, wherein said pressure plate is forced by said adjuster in a direction toward said anvil, and at least two bearings, said bearings responding to a movement of said pressure plate by exciting a force on said anvil in the same direction as the movement of said pressure plate.

4. The method of claim 2, wherein controlling an amount of pressure is accomplished using a force adjuster, said force adjuster comprising an adjuster, a pressure plate connected to said adjuster, wherein said pressure plate is forced by said adjuster in a direction toward said anvil, and at least two bearings, said bearings responding to a movement of said pressure plate by exerting a force on said anvil in the same direction as the movement of said pressure plate.

* * * * *